(12) United States Patent
Saunders

(10) Patent No.: US 10,131,629 B2
(45) Date of Patent: Nov. 20, 2018

(54) PROCESS FOR PRODUCING AJOENE

(71) Applicant: Neem Biotech Limited, Abertillery (GB)

(72) Inventor: Robert Alun Saunders, Abertillery (GB)

(73) Assignee: Neem Biotech Ltd, Gwent (GB)

( * ) Notice: Subject to any disclaimer, the term of this patent is extended or adjusted under 35 U.S.C. 154(b) by 0 days.

(21) Appl. No.: 15/529,053

(22) PCT Filed: Nov. 18, 2015

(86) PCT No.: PCT/GB2015/053494
§ 371 (c)(1),
(2) Date: May 23, 2017

(87) PCT Pub. No.: WO2016/083781
PCT Pub. Date: Jun. 2, 2016

(65) Prior Publication Data
US 2017/0253559 A1    Sep. 7, 2017

(30) Foreign Application Priority Data

Nov. 25, 2014 (GB) .................................. 1420902.7

(51) Int. Cl.
*C07C 319/22* (2006.01)
(52) U.S. Cl.
CPC .................................. *C07C 319/22* (2013.01)
(58) Field of Classification Search
CPC ............................ C07C 319/22; C07C 323/65
See application file for complete search history.

(56) References Cited

U.S. PATENT DOCUMENTS 5,741,932 A    4/1998    Dressnandt et al.

FOREIGN PATENT DOCUMENTS

| CN | 101928735 | 12/2010 |
|---|---|---|
| ES | 8704453 | 12/1985 |
| RU | 2239630 | 11/2004 |
| WO | 20100100486 | 9/2010 |
| WO | 20120076016 | 6/2012 |

OTHER PUBLICATIONS

Chemistry Libre Texts (Chromatographic Columns, https://chem.libretexts.org/Core/Analytical_Chemistry/Instrumental_Analysis/Chromatography/Chromatographic_Columns, Jan. 2, 2014, pp. 1-4).*
Hamilton ("PRP-1, 100 Å Reversed Phase HPLC Columns", www.westernanalytical.com/pdf/PRP1, Apr. 3, 2007.*
International Search Report for parent application App. No. PCT/GB2015/053494, dated Jan. 26, 2016.
Great Britain Search Report for related application App. No. GB1420902.7, dated Aug. 25, 2015.

* cited by examiner

*Primary Examiner* — Rosalynd A Keys
(74) *Attorney, Agent, or Firm* — Boulware & Valoir

(57) ABSTRACT

The present invention relates to a process for producing ajoene from allicin via a polymeric substrate, comprising the steps of heating allicin or an allicin solution at a predetermined temperature range such that at least a portion of the allicin is converted to ajoene to form an ajoene solution; and separating the ajoene from the ajoene solution; wherein at least one of the heating or separating steps is conducted via a polymeric substrate. The process for producing ajoene from allicin via a polymeric substrate further comprises a step of retaining the allicin or the allicin solution on the polymeric substrate before the heating step is conducted within or out of the polymeric substrate. The present invention also relates to ajoene or a composition comprising ajoene obtained by the process thereof.

18 Claims, No Drawings

PROCESS FOR PRODUCING AJOENE

TECHNICAL FIELD

The present invention relates to a process for producing ajoene and a composition comprising ajoene thereof. More particularly, the present invention relates to a process for producing ajoene from allicin via a solid phase polymeric substrate, and a composition comprising ajoene obtainable by the process thereof.

BACKGROUND OF THE INVENTION

Garlic, also known as *Allium sativum*, is a species in the onion genus, which has been commonly used worldwide as a culinary herb or nutraceutical foodstuff. There have been numerous medical properties ascribed to garlic for the treatment or prevention of various metabolic disorders or infections. It has also been used in folk medicine for thousands of years.

Garlic, in its fresh or crushed form, contains various types of derivatives, which includes the sulphur-containing compounds that contribute to its distinctive smell and taste, and non sulphur-containing compounds. Allicin is thought to be one of the major chemical compounds of garlic that is responsible for much of the odour and biological activity of garlic. Allicin is a chemically unstable, colourless to straw-coloured oil, converted from its precursor alliin [(+)(S-allyl-L-cyteine sulfoxide)] by the enzyme alliinase. An intact garlic clove does not contain allicin but rather its odourless precursor alliin. As alliin and alliinase are found in different compartments of the garlic clove, allicin is only converted into allicin when the cutting or crushing of the clove releases the alliinase and allows it to come into contact with alliin. Allicin is both unstable and volatile, and would naturally be converted to approximately 15 different metabolites depending on the media in which it is converted. These metabolites include diallyl disulphide, diallyl trisulphide, vinyl dithiins, ajoene and others. A method for preparing allicin in high yield and volume is described in EP 1404853 A1, part of the contents of which are herein incorporated by reference.

Ajoene is among one of the important garlic metabolites that is presently of interest in a number of fields of endeavour, including both human and animal pharmaceuticals. It has been documented in the art that ajoene possesses a wide range of medicinal properties, including antioxidants, anti-thrombotic, broad-spectrum antimicrobial, prevention of yeast infection, and inhibition of gene-controlling quorum sensing activities. However, the study and hence the use of ajoene for such purposes has been curtailed since the existing methods available for producing ajoene have low selectivity for ajoene. Consequently, ajoene is expensive to produce and only in relatively low yields.

There have been a few existing technologies described in the prior art related to the process for producing ajoene. For example, U.S. Pat. No. 5,612,077(A) describes a method to produce a macerate containing mainly Z-ajoene using edible oil, but in small volumes and low concentration. Another U.S. Pat. No. 5,741,932(A) describes a method of preparing ajoene using cyclodextrin, which is a complicated multi-step method and yet it produces small volumes of ajoene at a low concentration. Other approaches to ajoene production from allicin, such as that described in PCT publication No. WO/2010/100486 and Block et al. *Am Chem. Soc.,* 1986, 108 (22), have required the use of large volumes of volatile hydrocarbon solvents that may not be suitable to be used in production of food or herbal extracts. The solvent extraction approach of ajoene is also labour-intensive and costly.

In view of the various medicinal or therapeutic benefits of ajoene and ajoene-containing composition, it is desirable for the industry to provide an improved and innovative process for producing ajoene to overcome the drawbacks of the existing technologies.

SUMMARY OF THE INVENTION

One of the objects of the present invention is to provide a cost-effective process for producing ajoene from its precursor allicin, which is capable of achieving a high yield, high volumes and at reasonable costs.

Another object of the present invention is to develop an innovative process for producing ajoene or ajoene-containing compositions that involves the transition of conventional technology of solvent-based extraction to solid phase extraction.

Yet another object of the present invention is to provide a process for producing ajoene or ajoene-containing compositions, which is ideally solvent-free or requires a reduced amount of volatile hydrocarbon solvents, thus being less labour-intensive and reducing production costs.

Still another object of the present invention is to provide a process for producing ajoene or ajoene-containing compositions that is suitable for the mass preparation of ajoene to be further used in a large or industrial scale production of ajoene-containing products.

A further object of the present invention is to provide food-grade ajoene or ajoene-containing compositions via a process which is solvent-free or requires a reduced amount of volatile hydrocarbon solvents, thus providing ajoene or ajoene-containing compositions which are food-safe and/or suitable to be processed into various consumables or healthcare products.

At least one of the preceding objects is met, in whole or in part, by one or more of the embodiments of the present invention.

In a first aspect the present invention provides a process for producing ajoene from allicin via a solid phase polymeric substrate, comprising the steps of heating allicin or an allicin solution such that at least a portion of the allicin is converted to ajoene to form an ajoene solution; and separating the ajoene from the ajoene solution; wherein at least one of the heating or separating steps is carried out using the solid phase polymeric substrate.

The solid phase polymeric substrate can be a stationary phase of a chromatography column, such as a solid phase extraction (SPE) chromatographic column, or can be dispersed in a free-flowing form directly into a liquid. The polymeric substrate is preferably a microporous resin, more preferably, a polystyrene-divinylbenzene (DVB) copolymer resin.

The process for producing ajoene from allicin via a solid phase polymeric substrate can further comprise a step of retaining the allicin or the allicin solution on the polymeric substrate before the heating step is conducted within the polymeric substrate. Preferably, the process further comprises a step of removing water-soluble components and non-polar components from the allicin solution such that substantially pure allicin is retained by the polymeric substrate. The water-soluble components can be removed by passing a polar aqueous solvent through the polymeric substrate; whereas the non-polar components can be removed by passing a non-polar solvent through the polymeric substrate. Removal of water-soluble and non-polar components preferably results in substantially pure allicin being retained by the polymeric substrate. The allicin retained on the polymeric substrate may be at least 50% pure or at least 60% pure or more.

The allicin or the allicin solution may be obtained from a natural, synthetic or semi-synthetic source. Preferably, the allicin solution contains 0.1% w/v to 10% w/v of allicin.

The heating step for the conversion of allicin to ajoene can be conducted within the polymeric substrate, with or without an additional solid support, under a thermostatically controlled gas or liquid environment, or in a thermally insulated chamber. Preferably, the gas or liquid used is a hydrocarbon solvent, water or a combination thereof. Alternatively, the heating step for the conversion of allicin to ajoene may be conducted out of the polymeric substrate in a solvent. Preferably, the solvent is an alcohol, an ether, a ketone or a combination of two or more thereof.

The heating step can be conducted at a predetermined temperature range of from 15° C. to 90° C. Preferably, the predetermined temperature range is 30° C. to 80° C. Through the heating step, at least a portion of the allicin is converted to ajoene to form an ajoene solution. The at least a portion of the allicin may be at least 10% w/v, preferably at least 20% w/v or at least 30% w/v, more preferably at least 40% w/v. In preferred embodiments of the invention, at least 50% w/v of the allicin is converted to ajoene.

The separating step of ajoene after the conversion can be conducted under a predetermined pressure using a non-aqueous polar solvent, liquid or supercritical carbon dioxide ($CO_2$). Preferably, the process for producing ajoene from allicin via a polymeric substrate further comprises a step of concentrating the ajoene to form an ajoene-rich oil after the separating step. The ajoene-rich oil is brown in colour. Preferably the ajoene-rich oil contains 10% w/v to 30% w/v of ajoene.

In a second aspect the present invention provides ajoene or a composition comprising ajoene obtained by the process of the invention.

One skilled in the art will readily appreciate that the present invention is well adapted to carry out the objects and obtain the ends and advantages mentioned, as well as those inherent therein. The embodiments described herein are not intended as limitations on the scope of the invention.

DETAILED DESCRIPTION OF THE INVENTION

Hereinafter, the invention shall be described according to preferred embodiments of the present invention and by referring to the accompanying description. However, it is to be understood that limiting the description to the preferred embodiments of the invention is merely to facilitate discussion of the present invention and it is envisioned that those skilled in the art may devise various modifications without departing from the scope of the appended claim.

The present invention discloses a process for producing ajoene from allicin via a solid phase polymeric substrate, comprising the steps of heating allicin or an allicin solution such that at least a portion of the allicin is converted to ajoene to form an ajoene solution; and separating the ajoene from the ajoene solution; wherein at least one of the heating or separating steps is carried out using the solid phase polymeric substrate.

The presence of allicin and/or ajoene in a reaction mixture of the process, as well as the conversion of allicin to ajoene in the process, can be detected or monitored via a high performance liquid chromatography (HPLC) analysis. The general procedure of a HPLC analytical method can be found in the art, whilst detailed HPLC parameters that can be used in processes of the present invention are listed in Examples 1 to 3. Example 1 details the parameters used in a reverse phase HPLC method for the calibration and determination of allicin via a standard allicin solution. Example 2 details the parameters used in a reverse phase HPLC method for the calibration and determination of ajoene via a standard ajoene solution. A normal phase HPLC method for the determination of E/Z isomers of ajoene, calibrated via a standard ajoene solution, is detailed in Example 3.

The present invention produces ajoene or a composition comprising ajoene using a solid phase polymeric substrate instead of solvents, especially hydrocarbon solvents.

In a preferred embodiment of the present invention, the process for producing ajoene from allicin via a solid phase polymeric substrate includes minimum use of hydrocarbon solvents, or does not include the use of hydrocarbon solvents.

The solid phase polymeric substrate is preferably a microporous resin. By resin it is meant a fine powder or spherical beads comprised of organic polymers, and having micro and meso pore structure and specific functional groups suitable for absorption of specific compounds. More preferably, the microporous resin is polystyrene-DVB copolymer resin. Most preferably, the polymeric substrate is a hyper cross-linked hydroxylated polystyrene-DVB resin. However, other types of resin having similar chemical and physical properties, such as hydrophobic properties, can also be used as the polymeric substrate of the present invention. The resin used can be in the form of a fine powder or a spherical bead. Preferably the resin has a micro and meso pore structure and is able to effect sorption of the allicin and either subsequent conversion to ajoene or extraction into a soluble organic phase. Preferably, the resin has a permanent developed rigid pore structure.

The microporous resin of choice can either be synthesized from its monomers or commercially obtained. In order to obtain resins of high mechanical strength along with intricate pore structure with high surface area, suspension polymerisation can be used as the method of choice owing to the ease of scale up application. The general principle employed to synthesize these types of polymer resins can involve polymerisation of a styrene—DVB mixture with the co-monomer mixture, as well as an appropriate organic solvent (diluent or porogen). In particular, removal of the solvent or porogen at the end of the polymerisation leads the resin to form beads that are hard but opaque. The polymer matrix thus formed is heterogeneous or non-uniform. Most importantly, these materials can have much higher surface areas in the dry state than gel-type resins, as measured by the Brunauer-Emmett-Teller (BET) test, which is typically ranging around 1000 m$^2$/g. In view of the rigidity of these types of resins, they do not need to swell in a solvent to allow access to the interior because they possess a permanent porous structure and network of pores, in which the dimensions can be manipulated by the precise conditions used in the polymerisation process.

The hyper cross-linked hydroxylated polystyrene-DVB resin, such as ISOLUTE ENV+ from Biotage, which is a type of the polymeric resin of similar molecular structure and properties, is commercially available and can be used in the present invention. The polystryrene-DVB can also be synthesized using a general procedure such as that detailed in Example 4. Preferably, the procedure involves the use of a flange flask, a reflux condenser and a water bath, under a nitrogen condition. The monomer materials for the polystyrene-DVB resin, such as styrene, p-divinyl benzene and vinyl pyridine, can be mixed with one or more surfactants added to the mixture at different stages. The surfactant used can be Span 80, sodium sulphate, sodium dodecyl sulphate (SDS) or a combination of two or more thereof. They are used to keep the dispersion of the droplets within the solution and to ensure the particle size of the resin. An antioxidant, such as hydroquinone, can be added to quench the free radicals. The polymerization reaction of the resin can be initiated using an initiator, which is preferably to be benzoyl peroxide. Other initiators, such as azobisisobutyronitrile (AIBN), butyl peroxide or sodium persulphate, can also be employed, whereby suitable surfactant also has to be used according to the type of initiator used. Reaction solvent used for the polymerization mixture can be toluene, cyclyhexanol, xylene or others.

The reaction temperature of the synthesis of resin can be of about 70° C. to about 90° C., preferably at about 80° C. The polymerisation process can be allowed to proceed for approximately 12 to 48 hours, preferably for about 24 hours. The resin can be collected and cleansed, and then dried at about 70° C. to about 90° C., preferably at about 80° C. for approximately 5 hours. The resin can then be sized and beads with desired particle size, for example about 1 mm, can be collected. The resin collected is preferably subjected to physical parameters determination by BET test and electronic microscopy.

As detailed in Examples 5 and 6, the general procedure of Example 4 can be repeated in order to obtain a larger amount of the resin, as well as resin with different particle sizes. The suitable particle size of the resin can be ranging from about 75 µm to about 1200 µm in diameter. Particle size can be determined by a number of conventional methods, for example by particle analyzer. Variations of the resin synthesis methods and analysis are further detailed in Examples 4 to 15.

As set forth in the preceding description, allicin is used as the precursor in the process for producing ajoene of the present invention. The use of allicin of different sources for the production of ajoene is further detailed in Examples 16 to 24. Accordingly, the allicin or the allicin solution can be obtained from a natural, synthetic or semi-synthetic source. More preferably, allicin is obtained from a high yield preparation method, which is a semi-synthetic source as described in Example 16. Through the high yield preparation method of allicin, the precursor alliin that is derived from a natural garlic source is converted by the enzymatic reaction of alliinase to form allicin. Examples 21 and 22 detail the use of allicin obtained from a synthetic route. As detailed in Example 21, synthetic allicin can be produced via the oxidation of technical grade diallyl disulphide with peracetic acid. This method of production of allicin is well known in the art. However, peracetic acid may leave large amounts of acetic acid in the reaction solution, which requires additional steps and costs for removing it therefrom. Therefore, a more practical method for the synthetic production of allicin may be via the oxidation of technical grade diallyl sulphide in ethanol with an aqueous solution of potassium peroxymonosulfate, as detailed in Example 22.

On the other hand, allicin can also be produced directly via a natural route by crushing or macerating fresh garlic to obtain the allicin-containing garlic juice, which is as detailed in Example 23. This method may not be able to obtain a high yield of allicin. A person skilled in the art shall note that higher concentration of allicin in an allicin solution will give rise of a higher yield of ajoene in the process for producing ajoene. Preferably, the allicin solution contains about 0.1% w/v to about 10% w/v of allicin. Typically, the allicin concentration is ranging from about 0.5% w/v to about 2.5% w/v.

The starting allicin solution can contain at least 1,000 ppm of allicin. Preferably, the allicin solution contains at least 10,000 ppm of allicin. The allicin solution obtained via the natural or the semi-natural route typically comprises less than approximately 25,000 ppm of allicin. However, the allicin obtained from a synthetic route may be able to achieve a high concentration of more than 100,000 ppm. Alternatively, a pre-treatment process can also be conducted to concentrate the allicin obtained by the natural or semi-natural route in order to acquire allicin solution of such high concentration.

In order to obtain high purity of allicin, a further purifying step of allicin, such as that further detailed in the Example 18, can also be conducted after the allicin content is determined by HPLC. The allicin-rich fractions identified by HPLC can be dried and concentrated by a drying agent, for example magnesium sulphate, and filtered, before it is reduced by a reducing agent using an evaporator. The calibration of the allicin using a standardized allicin solution can be performed according to the HPLC method as detailed in Example 1.

The process for producing ajoene from allicin via a solid phase polymeric substrate can be initiated with a step of retaining the allicin or the allicin solution on the polymeric substrate.

This step can be conducted by passing the allicin or allicin solution through the polymeric substrate, which is can be a resin, such that the allicin is adhered onto the solid phase polymeric substrate. This process is capable of removing more than 90% of the water content from the allicin solution. The resin can be a stationary phase of a chromatography column, such as a SPE chromatographic column. Example 16 details one of the exemplary methods for the loading of allicin into a column. As described in the Example 16, the resin can be loaded into a column and cleansed with water. Allicin can then be flowed through the resin bed, preferably facilitated by a pumping means, such as a peristaltic pump, at a desired flow rate. Preferably, the flow rate of the column is about 20 ml to about 50 ml, preferably about 30 ml, per minute, in which the flow of the allicin solution can be set against gravity. The polarity of the allicin is low, hence it is able to be retained on the resin. An HPLC method can be used to monitor the eluent of the column in order to ensure that a bulk of allicin had adhered to the resin within the column. Suitable column, amount of allicin loaded and related conditions are further detailed in exemplary method of Example 16.

Preferably, a step of removing other water-soluble components from the allicin solution can be conducted such that the resin retains substantially pure allicin. The necessity of this step is to isolate allicin in high yield from any other water-soluble components and non-polar components that may affect the subsequent conversion of allicin to ajoene. The water-soluble components include, but are not limited to, alliin, deoxyalliin, pyruvate, sugars, water-soluble amino acids and protein, can be removed by passing a polar aqueous solvent, such as a highly polar aqueous solvent over the column; whereas the non-polar components such as diallyl polysulphides and plant oils, can be removed by passing a very non-polar solvent through the resin. As detailed in Example 16, deionized water can be used as the polar aqueous solvent for the removal of residual water-soluble components. It can be pumped through using the pumping means set at the same flow rate and direction as the allicin loading. The efficacy of the water-soluble components removal step can be monitored by HLPC and by the UV absorption spectrum of alliin, deoxyalliin, pyruvate, allicin and ajoene. Removal of water-soluble and non-polar components preferably results in substantially pure allicin being retained by the polymeric substrate. The allicin retained on the polymeric substrate may be at least 50% pure or at least 60% pure or more.

The resin can also be used without any solid support or in a free-flowing form, for example, in a dispersive method. In order to be used in a dispersive method, the allicin is preferably subjected to a centrifugation process to remove any solid particulate therefrom, and then the allicin liquid is dispersed free-flowingly in the resin beads. The reaction mixture of allicin and resin is to be kept cold at a predetermined temperature range of below 10° C. throughout the dispersion process. The allicin content is preferably determined using the HPLC method of Example 1. The dispersive method is further detailed in Example 19. This method is especially useful for large-scale production of the same.

As set forth in the preceding description of the present invention, the conversion of allicin to ajoene can occur via a heating process. The heating step for the conversion of allicin to ajoene can be conducted within the solid phase polymeric substrate, such as a polystyrene-DVB resin, under a thermostatically controlled gas or liquid environment, or in a thermally insulated chamber. Preferably, the gas or liquid used is a hydrocarbon solvent, water or the combination thereof. The pH of the thermostatically controlled liquid can be adjusted with the addition of any suitable acid or base to improve the reaction or selectivity. More preferably, a thermostatically controlled water tank is used for the heating process as it offers a better thermal distribution and is suitable to be used in a large-scale production. The resin column can be connected via the pumping means to a thermostatically controlled water tank to form a closed loop system. An exemplary method of using thermostatically controlled water tank for the heating process is further detailed in Example 16.

Additionally or alternatively, the resin column can be heated via a reflux method. As set forth in the preceding description, a hydrocarbon solvent, water or a combination thereof can be used for the reflux. The preferred hydrocarbon employed is acetone. Example 18 details the reflux-heating of the allicin-containing resin in a column. Example 24 further details the reflux-heating method which is equipped with a solvent recycling system, preferably inherent to a soxhlet extractor, which is capable of reducing the solvent used, as well as to remove the allicin from the resin at a later stage.

The heating step for the conversion of allicin to ajoene can be conducted with or without a solid support. Both the thermostatically controlled water tank or reflux methods are preferably performed on the allicin-containing resin within a solid support, such as a SPE column. Alternatively, the heating step can be conducted directly on the allicin-containing resin without any solid support, in a thermally insulated chamber, such as an oven incubator. This method is preferably used for the free-flowing allicin-containing resin obtained via the dispersive method. An exemplary method of the oven-heating is detailed in the Example 19. As described in Example 19, the resin can be placed on a metal tray and heated in the oven incubator. The conversion of allicin to ajoene can be monitored by HPLC, such as by the method of Example 2 using a sample of the resin after heating. The resin can be extracted using a solvent, such as methanol.

In the condition where the allicin is retained in the resin within a solid support before the heating step, for example the SPE column, an additional step can be applied to separate the allicin-containing resin from the column, should the oven-heating method is to be applied. Apart from that, allicin can also be removed from the resin without undergoing any conversion process, in order to be used for further processing of any allicin-containing products. In such condition, the column is used as a purifying device for the allicin-containing resin such that substantially pure allicin is obtained. An exemplary method for separating the allicin from the resin in a column is detailed in Example 18. A low boiling point non-polar solvent can be employed and facilitated with a negative pressure to the base of the column, in order to collect the allicin-containing solution. The preferred solvent used is diethyl ether.

The heating step can be conducted at a predetermined temperature range of about 30° C. to about 90° C. Preferably, the predetermined temperature range is about 30° C. to about 80° C. More preferably, the predetermined temperature range is about 40° C. to about 60° C. It is to be noted that, the heating temperature used for both heating methods with or without a solid support is similar. However, the time used for heating via a thermally insulated chamber without any solid support could be longer. Generally, the higher the temperature, the shorter the period of time required for the conversion of allicin to ajoene. The heating process can be conducted for a sufficient period of time, for example about 1 to about 15 hours for the conversion of at least a portion of the allicin to ajoene. Preferably, the sufficient period of time for the conversion is about 4 hours.

The extent of conversion from allicin to ajoene can be monitored by HPLC, for example as described in Example 2, and by UV absorption spectrum of allicin and/or ajoene. Preferably, the at least a portion of the allicin that has been converted into ajoene is at least 10% w/v, preferably at least 20% w/v or at least 30% w/v, more preferably at least 40% w/v. In preferred embodiments of the invention, at least 50% w/w of the allicin is converted into ajoene. The heating step may be conducted until at least 60%, or at least about 70%, or at least about 80%, or at least 90% of the allicin in the starting solution is converted to ajoene. Most preferably, substantially all of the allicin is converted to ajoene. By substantially all is meant that the heating step is continued until no further allicin is detected using an HPLC, such as that described in the method of Example 2.

As set forth in the foregoing description, the heating step for the conversion of allicin to ajoene, alternatively, can be conducted out of the polymeric substrate in a solvent. A solvent suitable for extracting allicin from the solid phase polymeric substrate, which can be a resin, for direct conversion to ajoene, is preferably a solvent that is suitable for solvating allicin and capable of providing the correct conditions for its conversion to ajoene. The solvent may be an alcohol, an ether, a ketone or a combination of two or more thereof. As set forth in the preceding description, the pH of the solvent can also be adjusted to improve the conversion of allicin to ajoene, as well as to adjust the E/Z ratio of the ajoene in the final product. As commonly known in the art, the pH can be adjusted with an organic or inorganic acid, or a base. A typically used pH adjusting acid is acetic acid.

The ajoene produced by the process of the present invention is to be separated from the solid phase polymeric substrate, which is containing ajoene, non-reacted allicin and other metabolites. In the condition where the heating process of allicin-containing resin is conducted in a free-flowing form without any solid support, an additional step of resin-packing can be conducted to load the heated resin into a solid support, such as a SPE column, for the subsequent separation process. Example 19 details such step of resin-packing into an extractor column. The oven-heated resin may be of higher moisture content, hence, it is preferable to freeze-dry the resin before it is packed into the column.

The separating step of ajoene can be conducted under a predetermined pressure using a non-aqueous polar solvent, such as liquid $CO_2$ or supercritical $CO_2$. Preferably, the non-aqueous polar solvent is acetone or other non-aqueous polar solvents such as methanol and ethyl acetate can also be used. However, highly polar solvents such as water, or non-polar solvents such as pentane and hexane, are not suitable to be used in this separating step. The separating step can be achieved by washing the column using the solvent, fed via gravity from the top of the column and collecting the eluent thereafter. The ajoene content of each fraction can be determined via HPLC, for example as described in the method of the Example 2.

Preferably, the process for producing ajoene from allicin via a solid phase polymeric substrate further comprises a step of concentrating the ajoene to form an ajoene-rich oil after the separating step. The ajoene-rich fractions as determined by HPLC, for example as described in the method of Example 2, can be combined and dried using a drying agent, such as anhydrous magnesium sulphide. The dried ajoene in the solvent can be filtered under gravity to remove any solid impurities. Preferably, the solution containing ajoene can be filtered through a Whatman paper filter. The solvent can then be reduced under vacuum at a predetermined pressure of about 400 torr (53.4 kPa) to about 150 torr (19.9 kPa) and a temperature range of about 56° C. to about 40° C. The temperature may be adjusted according to the different types of solvent used. Preferably, a rotary evaporator is used to facilitate the extraction of solvent. The process is further detailed in Example 16.

Besides the polar solvent, liquid or supercritical $CO_2$ is also suitable for use in extracting the ajoene from the resin, as these materials are all food-safe. The extraction can be carried out with supercritical $CO_2$ extraction at a predetermined pressure range of about 400 bar (40,000 kPa) to about 500 bar (50,000 kPa) and at a predetermined temperature range of about 40° C. to about 55° C. Sequential extraction using different concentrations of co-solvent, such as 10% and 20% ethanol using the same pressure and temperature can be applied and the resulting extracts may be analysed to ensure that a complete extraction has been achieved by the supercritical $CO_2$. Both the resulting extracts of the supercritical $CO_2$ and the resin can be analysed using HPLC, for example as described in the method of Example 2.

The ajoene solution yielded by the supercritical $CO_2$ can also be further processed by further extracting the yield at a different temperature, for example as detailed in Example 20, to form an emulsion, which is then separated into an aqueous layer and an oily layer. These layers can be analysed by HPLC, for example as described in the method of Example 2, and any allicin present in the oily layer can be further processed into allicin-rich products or to be further converted to ajoene using any of the methods as described in the present invention.

Other allicin metabolites formed in the conversion or naturally occurring garlic compounds such as fatty acids and hydrocarbons present in the final ajoene solution can also be removed using a suitable solvent in order to obtain ajoene of high purity. The ajoene-rich oil finally obtained preferably contains 10% w/v to 30% w/v of ajoene based on the total volume of the oily fraction. More preferably, the process of the present invention is capable of providing a highly concentrated and purified ajoene-rich oil of at least 15% w/v to 30% w/v of liquid in the oily fraction.

Ajoene exists in two isomer forms, which is cis (Z) and trans (E) form. The ajoene produced by the present invention will typically be isolated as a mixture of both isomers. HPLC, for example as detailed in Example 3, can be used to determine the E/Z ratio of the ajoene.

The ajoene obtained by the present invention via an aqueous acetone extraction is generally having an E:Z ratio of 1-2:3 as determined by the HPLC analysis. The yield and the E/Z ratio of ajoene can be affected by the temperature, duration, polarity and pH of the conversion media. The ajoene-rich oil of the present invention is suitable to be directly used in the formulation of ajoene products or to be further purified into pure E- or Z-ajoene using a method such as normal phase silica chromatography with a hexane-propanol mobile phase or any other suitable methods known to a person skilled in the art.

The present invention also provides ajoene or a composition comprising ajoene obtained by the process of the invention. The ajoene can be formulated into various types of products with therapeutic effects or health benefits. Via formulation with compounds such as multicrystalline cellulose, maltodextrin and cyclodextrins, physio-chemical properties of the ajoene and other garlic oil compounds such as odour, stability and solubility can be beneficially modified.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to, without departing from the scope of the invention.

EXAMPLES

Examples are provided below to illustrate different aspects and embodiments of the present invention. These examples are not intended in any way to limit the disclosed invention, which is limited only by the claims.

Example 1—Reverse Phase HPLC Conditions for the Calibration of Allicin Using a Standardised Allicin Solution Peak identification: Allicin @ 9.5 minutes
Column: Ace 5 C18
Dimensions: 250×4.6 mm
Guard Column: Ace 5 C18
Mobile phase: 50% methanol—50% water
Temperature: 30° C.
Detection wavelength: 210 nm (UV)
Sample volume: 20 µl Sample solvent: water
Flow rate: 1.0 ml/min Example 2—Reverse Phase HPLC Condition for the Calibration of Ajoene Using a Standardised Ajoene Solution Peak identification: ajoene (both E/Z eluted together) @ 6.5 minutes
Column used: ACE 5 C18
Dimensions: 250×4.6 mm
Guard Column: Ace 5 C18
Mobile phase: (Solvent A) water—(Solvent B) Acetonitrile
Flow rate: 1.5 ml/min
Gradient:

TABLE 1

| Minute | % Mobile Phase B |
|---|---|
| 3 | 45 |
| 13 | 45 |
| 18 | 80 |
| 18.01 | 45 |
| 22 | 45 |

Temperature: 30° C.
Detection wavelength: 254 nm (UV)
Sample volume: 20 µl
Sample solvent: Methanol Example 3—Normal Phase HPLC Condition for the Determination of Ajoene E and Z Isomers Calibrated Using a Standardised Ajoene Solution Peak identification: Z ajoene @ 14 minutes; E ajoene @ 17 minutes
Column used: Silica
Dimensions: 250×4.6 mm, manufactured by NN Scientific Ltd.
Mobile phase: 92% Hexane—8% 2-Propanol
Temperature: 30° C.
Detection wavelength: 240 nm (UV)
Sample volume: 20 µl Sample solvent: 2-Propanol
Flow rate: 1.0 ml/min Example 4—Preparation of the Polymeric Substrate (Copolymer Resin of Polystyrene-Divinylbenzene)

To a flange flask fitted with an overhead stirrer and an anchor shaft, an inlet for nitrogen, a reflux condenser and a water bath was introduced deionised water (100 g). Dry nitrogen was bubbled through the aqueous layer. To this stirred solution was added hydroquinone (0.01 g) followed by sodium sulphate (0.02 g) and a surfactant (SDS, 0.015 g). Previously mixed solution of styrene (4 g), p-divinyl benzene (2 g), vinyl pyridine (0.5 g), Span 80 (1 g) and benzoyl peroxide (0.5 g) in toluene (20 ml) was added drop wise over 30 minutes. The mixture was stirred at 200 rpm and the temperature of the reaction mixture was raised to 80° C. The inlet of the nitrogen was raised above the surface of the reaction mixture and the polymerisation was allowed to proceed for 24 hours. At the end of this period the resin was collected by filtration and washed successively with water followed by ethanol. The resin was dried at 80° C. for 5 hours. The resin was sized and beads with particle size of 1 mm were collected (yield 2.5 g). Physical parameters of the beads were determined by BET and by electronic microscopy.

Example 5—Preparation of the Polymeric Substrate (Copolymer Resin of Polystyrene-Divinylbenzene)

The experiment as detailed in Example 4 was repeated such that approximately 500 g of the resin was obtained after series of experimental manipulation. The nominal particle size of the resin varied between 800-1200 µm and had a surface area of 1200 m$^2$/g.

Example 6—Preparation of the Polymeric Substrate (Copolymer Resin of Polystyrene-Divinylbenzene)

The experiment as detailed in Example 4 was repeated except that the emulsification speed of the stirrer was increased to 1000 rpm to obtain resins with a particle distribution of 75-190 µm. A sample of this resin was used to evaluate initial sorption studies.

Example 7—Preparation of the Polymeric Substrate (Copolymer Resin of Polystyrene-Divinylbenzene)

The process for the preparation of the resin as detailed in Example 4 was repeated, but the initiator was replaced with AIBN in toluene (40 ml). A dark resin (450 g) was obtained after sizing the formed beads elutropically. The dried material was washed successively with water and acetone to remove any residual soluble. This resin showed excellent sorption and desorption characteristics towards the analyte.

Examples 8-15—Preparation of the Polymeric Substrate (Copolymer Resin of Polystyrene-Divinylbenzene)

The experiment as detailed in Example 4 was repeated using different substrates or parameters as tabulated in Table 2.

TABLE 2

| Substrates/Parameters | Example 8 | Example 9 | Example 10 | Example 11 | Example 12 | Example 13 | Example 14 | Example 15 |
|---|---|---|---|---|---|---|---|---|
| Styrene (g) | 4 | 4 | 4 | 4 | 4 | 4 | 4 | 4 |
| Divinyl benzene (g) | 2.6 | 2.6 | 2.6 | 2.6 | 2.6 | 2.6 | 2.6 | 2.6 |
| Vinyl Pyridine (g) | 1 | 0 | 1 | 1 | 1 | 1 | 1 | 1 |
| SDS (g) | 0.015 | 0.015 | 0.015 | 0.015 | 0.015 | 0.015 | 0.015 | 0.015 |
| Sodium sulphate (g) | 0.02 | 0.02 | 0.02 | 0.02 | 0.02 | 0.02 | 0.02 | 0.02 |
| Benzoyl peroxide (g) | 0 | 0 | 0 | 0 | 0 | 0.5 | 0 | 0 |
| AIBN (g) | 4 MI | 4 MI | 0 | 0 | 4 mL | 0 | 0 | 0 |
| Butyl peroxide (g) | 0 | 0 | 0 | 1 | 0 | 0 | 1.5 | 1.5 |
| Sodium persulphate (g) | 0 | 0 | 1 | 0 | 0 | 0 | 0 | 0 |

TABLE 2-continued

| Substrates/Parameters | Example 8 | Example 9 | Example 10 | Example 11 | Example 12 | Example 13 | Example 14 | Example 15 |
|---|---|---|---|---|---|---|---|---|
| Temperature (° C.) | 80 | 80 | 80 | 80 | 80 | 80 | 80 | 80 |
| Stirring Speed (rpm) | 200 | 200 | 200 | 200 | 200 | 200 | 200 | 200 |
| Hydroquinone (g) | 0.01 | 0.01 | 0.01 | 0.01 | 0.01 | 0.01 | 0.01 | 0.01 |
| Polyvinyl alcohol (ml) | 1.0 | 1.0 | 1.0 | 1 | 1 | 1 | 1 | 1 |
| Toluene (ml) | 0 | 0 | 0 | 20 | 0 | 0 | 20 | 0 |
| Cyclyhexanol (ml) | 20 | 20 | 20 | 0 | 0 | 0 | 0 | 0 |
| Xylene (ml) | 0 | 0 | 0 | 0 | 20 | 20 | 0 | 20 |
| Water (ml) | 100 | 100 | 100 | 100 | 100 | 100 | 100 | 100 |
| Yield (% wt) | 70 | 55 | 60 | 75 | 55 | 50 | 60 | 65 |

Example 16—Preparation of Ajoene from Allicin 90 g of resin were loaded into a glass column of dimension 3×38 cm. The resin was washed with 200 ml of deionized water. 1500 ml of a 15,000 ppm allicin solution manufactured using the method as detailed in Patent No. EP 1404853 A1, were flowed through the resin bed using a Cole Palmer Master Flex peristaltic pump. The pump was set at a flow rate of 30 ml per minute. The flow of the allicin solution was set against gravity. Aliquots of the eluent were monitored by HPLC using method as detailed in the Example 1. The HPLC results revealed the bulk of allicin had adhered to the column. The allicin-loaded resin was then washed with 500 ml of deionized water to remove residual water-soluble components. The water was pumped through using the peristaltic pump set at the same flow rate and direction as the allicin loading. The resin column was then connected via the peristaltic pump to a thermostatically controlled water tank to form a closed loop system. The tank water temp was set at 57° C.+−2. The heated water was circulated at the same flow rate and direction as the allicin loading for a period of 3 hours. The column was then washed with 600 ml of acetone; the acetone was fed via gravity from the top of the column and collected in 100 ml aliquots. The ajoene content of each fraction was determined via HPLC method as detailed in Example 2. The ajoene-rich fractions (fraction 2-5) were combined and dried using anhydrous magnesium sulphate. The dried ajoene-containing acetone was then filtered through paper under gravity to remove any solid. The acetone was reduced under vacuum at 50° C. using a Buchii RE300 rotary evaporator. 16 g of light orange oil were obtained. The oil was scanned using HPLC method of Example 2 and determined to have an ajoene content of 18%. The ajoene was determined to have a Z/E ratio of 2.3 using the HPLC method as detailed in the Example 3.

Example 17—Preparation of Ajoene from Allicin

The method as detailed in Example 16 was employed to absorb 1500 ml of a 15,000 ppm allicin onto 90 g of resin and to convert the allicin to ajoene using a circulating flow of hot water. The absorbed ajoene was then washed off from the column using 900 ml of ethanol. The ethanol was collected in 100 ml aliquots. The ajoene content of each fraction was determined via HPLC as detailed in Example 2. The ajoene rich fractions (3-6) were combined. The combined fractions were reduced under vacuum at 60° C. using a Buchii rotary evaporator. A 40 ml aqueous solution with an oily residue was collected, and was then separated into district bi-layers using a Beckman centrifuge set a 2000 rpm for a period of 20 minutes. The oil and water layers were then separated using a 200 ml separating funnel. 15 ml of oil with an ajoene content of 17.5% as determined using HPLC method of Example 2 was obtained.

Example 18—Preparation of Ajoene from Allicin 1600 ml of 15,000 ppm allicin was loaded onto a resin column as described in Example 16. The allicin solution was chilled to <10° C. to preserve the allicin. The column was then washed with 1000 ml of deionized water chilled to <10° C. 500 ml of diethyl ether was applied to the top of the column and negative pressure was applied to the base to collect the liquid. The diethyl ether was collected in 100 ml aliquots. Each of the fractions was collected and the allicin content was determined with HPLC method of Example 1. The allicin-rich fractions (1-6) were combined and dried with magnesium sulphate. The diethyl ether was then filtered under gravity through a Fluted Whatman 113 Grade filter paper. The Ether was then reduced to light yellow oil using a Buchii RE300 rotary evaporator at 20° C. 10.5 ml of light yellow oil was obtained and analysis with HPLC determined a purity of 90%. The pure allicin was diluted in a 200 ml volume of 60% acetone and refluxed at 56° C. for a period of 3.5 hrs. After reflux the acetone was removed under vacuum using a Buchii RE300 rotary evaporator. An aqueous solution containing a light orange oil was obtained. The light orange oil was removed using a separating funnel. The oil (9 g) was analysed using HPLC methods 2 and 3, it was determined to have an ajoene content of 21% and a Z/E ratio of 1.3.

Example 19—Preparation of Ajoene from Allicin 1500 ml of 15000 ppm allicin was prepared using the method as detailed in Patent No. EP 1404853 A1. The allicin liquid was centrifuged at 2000 rpm for a period of 20 mins using a Beckman J6B to remove any solid particulate. The liquid was then gently stirred with 110 g of resin in a 4000 ml beaker. A slow stirring speed sufficient to disperse the resin throughout the liquid was achieved using a magnetic stirrer. The liquid was stirred for a period of 4 hours and temperature was kept below 10° C. by the periodic addition of crushed ice to the reaction mixture. After 5 hours, the allicin content of the liquid was determined to be <1000 ppm using HPLC method of Example 1. The liquid and the resin were then separated via vacuum filtration using a Whatmann 113 Grade paper filter. The resin was washed under vacuum with 1000 ml of cold deionized water while still in the filter. The resin was then placed on a sealed metal tray and heated at 50° C. in an oven incubator for a period of 10 hours. The conversion of allicin to ajoene was monitored by taking 10 mg samples of resin extracting with 1 ml of methanol and scanned using HPLC method of Example 2. After conversion was complete the resin was transferred to an Edwards Super Modulyo freeze dryer and then dried to constant weight. The moisture content of the resin pre-freeze drying was determined to be 40%. 40 g of freeze-dried resin were packed into a 100 ml extractor, fitted to a Thar SFC-1000 laboratory rig, with a 25 ml separator maintained at 15 bar and 35° C. Extraction was carried out with supercritical $CO_2$ extraction for 3 hours at 400 bar and 40° C. followed by sequential extraction with 10% and 20% ethanol used as co-solvent using the same pressure and temperature. The separator was washed with ethanol and the solution retained. The extractor was then emptied and the extracted resin retained. The extracts and the resin were analysed using HPLC method of Example 2. Analysis of the extracts with 10% ethanol as co-solvent showed that most of the vinyl dithins and sulphides had been extracted with supercritical $CO_2$ alone and the co-solvent extracts were predominately ajoene. The 20% ethanol co-solvent showed that the 10% addition was sufficient as almost no ajoene was left to extract. Analysis of the residual resin post extraction showed that a complete extraction of ajoene had been achieved.

Example 20—Preparation of Ajoene from Allicin 62 g resin loaded with allicin was prepared using the dispersive method as detailed in Example 19. The allicin was washed with cold deionized water but no heat was applied to begin the conversion. The resin (62 g) was packed into a 100 ml extractor. This extra weight in comparison to that of Example 19 is attributed to the water content. Initial extraction was carried out using liquid $CO_2$ at 65 bar and 10° C. with a flow rate of 10 g/min for 2 hours. This yielded 0.111 g (0.184%) of allicin. The temperature was then raised to 40° C. and the pressure to 400 bar and extracted under supercritical conditions for a further 3 hours. 2.93 g of an emulsion were produced. On standing at room temperature, the emulsion separated into an aqueous layer and an oily bottom layer. HPLC Analysis of the extracted resin showed that the extraction had been successful and virtually no allicin remained on the resin. The oily layer was analysed with HPLC method of Example 2. The allicin-rich oil was suitable for further processing into allicin-rich products or conversion to ajoene by any appropriate methods detailed in any of the examples.

Example 21—Preparation of Ajoene from Allicin 25 ml of synthetic allicin was produced via the oxidation of technical grade diallyl disulphide with peracetic acid using the method detailed by Iberl et al (Plant Med 56 (1990). The allicin was then mixed vigorously with 2000 ml of water to produce an unstable emulsion that would begin to separate on standing. 90 g of resin were loaded into a column of dimension 3×38 cm. The synthetic allicin solution was then flowed through the resin bed using a Cole palmer master flex L/5 peristaltic pump. The pump was set at a flow rate of 40 ml per minute. The flow of the allicin solution was set against gravity. Aliquots of the eluent were monitored by HPLC method of Example 1. The HPLC revealed that the bulk of allicin had adhered to the column. The column was then connected via the bottom outlet to a side arm collection flask. Negative pressure was applied to the flask and 200 ml of deionized water was used to wash the column. Negative pressure was continually applied and air was allowed to flow through the column to remove excess moisture from the resin. The resin was then placed on an open metal tray and heated at 50° C. in a Raven oven incubator for a period of 10 hours. The conversion of allicin to ajoene was monitored by taking 10 mg samples of resin extracting with 1 ml of methanol and scanning using HPLC method of Example 2. After heating, the resin was a dry free-flowing solid. The resin was packed into a 3×40 cm column and 500 ml of pentane was washed over the column. Analysis of the pentane eluent showed predominantly vinyl dithin and polysulphides. The residue of solvent was then removed from the resin by passing positive pressure over the column and venting the exhaust. The column was then washed with 600 ml of acetone heated to 40° C.; the acetone was fed via gravity from the top of the column and collected in 100 ml aliquots. The ajoene content of each fraction was determined via HPLC method of Example 2. The ajoene rich fractions were combined and dried using magnesium sulphate. The dried acetone was then filtered through paper under gravity to remove any solid. The ajoene acetone was reduced under vacuum at 50 degrees using a Buchii rotary evaporator. 10 g of light orange oil were obtained. The oil was scanned using HPLC method of Example 2 and determined to have an ajoene content of 34%.

Example 22—Preparation of Ajoene from Allicin

Synthetic allicin (25 ml) was produced by the oxidation of technical grade diallyl disulphide in ethanol with an aqueous solution of potassium peroxymonosulfate. The aqueous salt solution was added drop wise over a period of 2 hours, temperature was kept below 30° C. and the solution stirred at all times. The conversion of diallyl disulphide to allicin was monitored via HPLC method of Example 2. After completion the reaction liquid was filtered through paper to remove salt. The filtered solution was diluted with deionized water to produce a 1000 ml 25,000 ppm allicin solution. The allicin solution was then loaded onto 90 g of resin packed in a column of dimension 4×38 cm and converted to ajoene in accordance with the procedure as detailed in Example 21. For the Oxone-derived allicin 3000 ml of deionized water was used to wash the allicin when absorbed onto the column to ensure that all salt had been removed.

Example 23—Preparation of Ajoene from Allicin 15 kg of fresh peeled garlic purchased from the local market was juiced using a Silvercrest centrifugal juicer. 10 L of juice was obtained which was then stirred with 10 L of potable water. The garlic solution was then clarified via centrifuge. The liquid was analysed by HPLC method of Example 1 and determined to have an allicin content of 1000 ppm. The garlic juice liquid was converted using the method as detailed in Example 16, with the following modifications. The allicin liquid was passed over the resin at a speed of 150 ml per minute. The eluent from the column was not discarded but instead fed into the allicin feed to create a closed loop system. The allicin feed tank was submerged in an ice bath to keep the temperature below 10° C. The allicin content of the tank was checked using HPLC method of Example 1 at 1-hour intervals. After six hours, no more allicin was absorbed onto the column, the flow was stopped and the column drained. Following this step, the treatment of washing and converting was identical to Example 16. The process yielded 20 g of light orange oil with an ajoene content of 15%.

Example 24—Preparation of Ajoene from Allicin 40 g of resin loaded with allicin was prepared as detailed in Example 19. The resin was the transferred into a 4.5×10 cm cellulose extraction thimble and mounted inside a suitably sized soxhlet extractor fitted with a water-cooled condenser and a 2 L round bottom flask mounted in an electromantle electric heating mantle. 500 ml of 40% aqueous acetone was placed round bottom flask. The acetone was gently heated to reflux and distilled through the resin in the method typically employed during a soxhlet extraction. After 1 hour, the cycling solvent returning from the resin in the siphon was seen to be clear. At this point the heating was stopped and the round bottom flask removed. The round bottom flask was then connected to a condenser and the solution was refluxed at 56° C. for a period of 1.5 hrs. After reflux, the acetone was removed under vacuum using a Buchii RE300 rotary evaporator. An aqueous solution containing light orange oil was obtained. The light orange oil was removed using a separating funnel. The light orange oil (10 g) was analysed using HPLC method of Examples 2 and 3, and was determined to have an ajoene content of 14% and a Z/E ratio of 3.1.

The invention claimed is:

1. A process for producing ajoene from allicin via a solid phase polymeric substrate, comprising:
   retaining allicin or an allicin solution on the polymeric substrate before the heating step is conducted;
   heating allicin or an allicin solution such that at least a portion of the allicin is converted to ajoene to form an ajoene solution; and
   separating the ajoene from the ajoene solution.

2. A process according to claim 1, further comprising a step of removing water-soluble components and non-polar components from the allicin solution such that allicin retained by the polymeric substrate is at least 50% pure.

3. A process according to claim 2, wherein the water-soluble components are removed by passing a polar aqueous solvent through the polymeric substrate.

4. A process according to claim 2, wherein the non-polar components are removed by passing a non-polar solvent through the polymeric substrate.

5. A process according to claim 1, wherein the allicin or the allicin solution is obtained from a natural, synthetic or semi-synthetic source.

6. A process according to claim 1, wherein the allicin solution contains 0.1% w/w to 10% w/w of allicin.

7. A process according to claim 1, wherein the heating step for the conversion of allicin to ajoene is conducted within the polymeric substrate, with or without a solid support, under a thermostatically controlled gas or liquid environment, or in a thermally insulated chamber.

8. A process according to claim 7, wherein the gas or liquid used is a hydrocarbon solvent, water or a combination thereof.

9. A process according to claim 1, wherein the heating step for the conversion of allicin to ajoene is conducted out of the polymeric substrate in a solvent.

10. A process according to claim 9, wherein the solvent is an alcohol, an ether, a ketone or a combination of two or more thereof.

11. A process according to claim 1, wherein the heating step is carried out at a predetermined temperature range of from 30° C. to 90° C.

12. A process according to claim 1, wherein at least 50% w/w of the allicin is converted to ajoene.

13. A process according to claim 1, wherein the separating step is conducted under a predetermined pressure using a non-aqueous polar solvent, liquid carbon dioxide or supercritical carbon dioxide.

14. A process according to claim 1, further comprising a step of concentrating the ajoene to form ajoene-rich oil after the separating step, wherein the ajoene-rich oil contains 10% w/v to 30% w/v of ajoene.

15. A process according to claim 1, wherein the polymeric substrate is in a stationary phase of a chromatography column or in a free-flowing form.

16. A process according to claim 1, wherein the polymeric substrate is a microporous resin.

17. A process according to claim 16, wherein the microporous resin is a polystyrene-divinylbenzene copolymer resin.

18. A process according to claim 1, wherein the process does not include the use of hydrocarbon solvent.

* * * * *